United States Patent [19]

Shishido

[11] Patent Number: 4,503,865

[45] Date of Patent: Mar. 12, 1985

[54] HARDNESS MEASURING PROBE

[75] Inventor: Yoshio Shishido, Sagamihara, Japan

[73] Assignee: Olympus Optical Co., Ltd., Tokyo, Japan

[21] Appl. No.: 452,040

[22] Filed: Dec. 22, 1982

[30] Foreign Application Priority Data

Dec. 28, 1981 [JP] Japan .............................. 56-212759
Dec. 28, 1981 [JP] Japan .............................. 56-212760
Dec. 28, 1981 [JP] Japan .............................. 56-212757

[51] Int. Cl.³ ................................................ A61B 5/10
[52] U.S. Cl. ......................................... 128/774; 73/78; 128/737
[58] Field of Search ................. 128/774, 737, 645; 73/78, 82

[56] References Cited

U.S. PATENT DOCUMENTS

| | | | |
|---|---|---|---|
| 3,150,521 | 9/1964 | Mackay et al. | 128/645 |
| 3,834,374 | 9/1974 | Ensanian | 128/639 |
| 4,364,399 | 12/1982 | Dashefsky | 128/774 |
| 4,373,397 | 1/1981 | Keller | 73/721 |

FOREIGN PATENT DOCUMENTS 353090 5/1922 Fed. Rep. of Germany .......... 73/82

Primary Examiner—Kyle L. Howell
Assistant Examiner—John C. Hanley
Attorney, Agent, or Firm—Kenyon & Kenyon

[57] ABSTRACT

This invention discloses a hardness measuring probe making it possible to continuously and quickly measure the hardness around an object position by a simple operation. The pressure around the object to be measured is led from an aperture to one pressure receiving surface and such rotating and contacting means as a roller is contacted with the object and the hardness of the object is measured on the other pressure receiving surface so that the hardness may be continuously and quickly measured by a simple operation.

9 Claims, 7 Drawing Figures

HARDNESS MEASURING PROBE

BACKGROUND OF THE INVENTION

This invention relates to a hardness measuring probe with which the hardness of an object to be measured can be continuously and quickly measured by a simple operation.

Recently, extensive use has been made of an endoscope with which the irregularity of an affected part or the state of a tumor can be observed with an elongated inserted part introduced into a body or cavity or, as required, a therapeutic treatment can be made by using a forceps.

However, with an endoscope, the hardness of a tumor or the state of a node in an affected part can not be detected.

Further, the hardness of the tumor in the above mentioned affected part is different depending on the kind and growth stage. Therefore, if such hardness is detected and is made data for the diagnosis, the diagnosis will be able to be made more accurate.

Heretofore, it has been known to use a pressure-sensitive element at the tip of a flexible bar-shaped member which can be advanced and retreated within a tubular member such as a forceps channel in an endoscope as is disclosed in the Gazette of the Japanese utility Model Publication No. 18371/1975.

In cases where the detection of variations in hardness of a normal part and an affected part abiut an object position depends on the degree of pressing, the measurement results, even in the same place will fluctuate. Also, there has been difficulty in repeating the contacting and separating operations. Further, there has been a defect that, unless the measuring intervals are carefully set, the necessary position will not be able to be measured.

In order to prevent the fluctuation of the measured result, it has been known to provide the pressure-sensitive element with a seat body of such shape as opens in the form of a cone to enclose the bar-shaped member to keep the force pressing the pressure-sensitive element constant in measuring the hardness as is disclosed in the Gazette of Japanese Utility Model Publication No. 18372/1975. In this example, if the surface to be measured is substantially flat, there will be no problem but, if it is a recessed surface of the irregularity, the surroundseat body will contact a projecting surface adjacent to the recessed surface, the pressure-sensitive element part will not be able to well contact the recessed surface and the measuring precision will reduce.

Further, unless the surrounding seat body is pressed against the surface to be measured in a uniformly contacting direction, the measured value will greatly fluctuate and the measuring direction will be restricted. Therefore, places where the pressure-sensitive element can be used are limited.

There is substantially the same problem even where a hood is provided on the outer periphery of the tip part of an endoscope as is disclosed in the Gazette of Japanese Utility Model Publication No. 18373/1975.

It has also been known to have a distortion gauge contained in a container fitted to the tip of an endoscope or the like with a presser fixed on the base side of the distortion gauge and is partly projected on the tip side out of the container as is disclosed in the Gazette of Japanese Patent Laid Open No. 98378/1977. Even in this example, there is substantially the same problem that, in such measuring position in which the surface of the container around the presser will contact a projection in the case of the measurement, it will be difficult to precisely measure the hardness of a recessed surface adjacent to the projection.

Also, in the prior art example disclosed in the Gazette of Japanese Utility Model Laid Open No. 51235/1980, unless the object position can be held, the hardness will not be able to be measured and therefore use will be greatly limited.

Further, it has been known to extend two flexible narrow plate-shaped members out in parallel with each other with distortion gauges fitted on each. In addition, one member is curved at the tip by 90 degrees and is passed through a slot-shaped incision formed at the tip of the other member so as to partly project at the curved tip as is disclosed in U.S. Pat. No. 4,132,224. In this example, in case the curved tip vertically presses an object position, the hardness will be able to be measured at a high precision but, for an object which can not be pressed from the vertical direction, the function will not be developed.

Further, this example is not well adapted to the measurement of the hardness within a living body as judged from the fact that, in this example, the surface vertical to the direction in which the plate members are parallelly expanded out can be measured and therefore the hardness of the surface of an affected part forward in the inserting direction which can be well observed with an ordinary straight sight type endoscope can not be observed.

Further, the above mentioned problems derive from the basic structures and are hard to simply solve.

Each of the above described prior art examples has problems in cases of measuring the hardness of an affected part or the like within a body cavity inflated with air. That is, if the atmospheric pressure around an affected part varies during the measurement, the atmospheric pressure acting on the pressure-sensitive element will appear as varied in the measured result and the pressure pressing the affected part will appear as varied in the measured result. Thus, much time will be required to precisely measure the hardness around the object position. Further, there is a problem that, in the measurement for a long time, the operation will be so difficult that the measurement will be likely to become rough.

BRIEF SUMMARY OF THE INVENTION

An object of the present invention is to provide a hardness measuring probe making it possible to measure the hardness in and around an object position with a simple operation.

Another object of the present invention is to provide a hardness measuring probe with which the hardness can be measured continuously at a high precision.

A further object of the present invention is to provide a hardness measuring probe with which the influence of the atmospheric pressure around an object to be measured can be considered.

Further objects and features of the present invention will become clear enough by the following explanation.

DETAILED DESCRIPTION OF THE PREFERRED EMBODIMENTS

Figure 1:
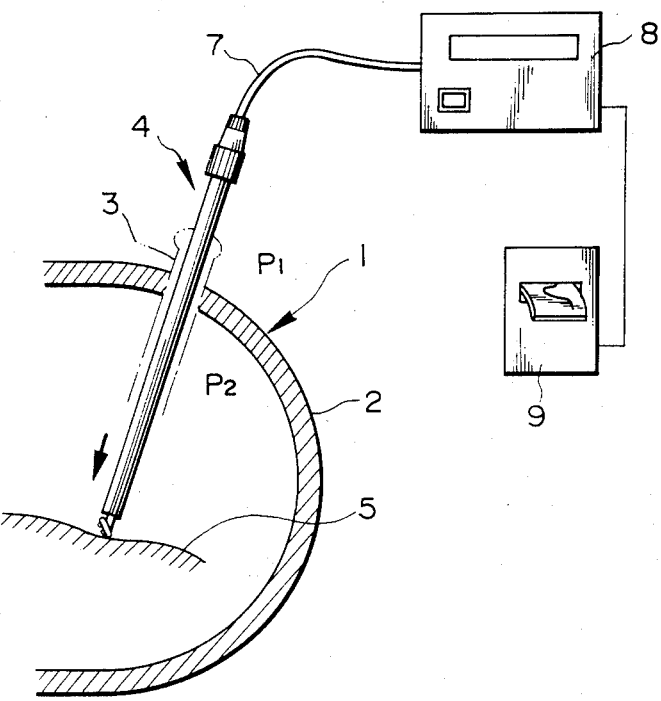
FIG. 1 is a schematic explanatory view showing the manner of measuring a hardness by using the first embodiment.
Figure 2:
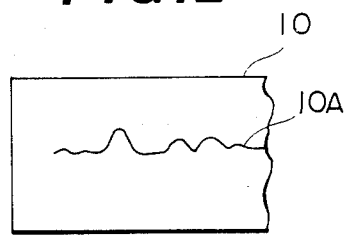
FIG. 2 is an explanatory view showing data measured by using the first embodiment.

First of all, the summary of the hardness measuring operation shall be explained. As shown in FIG. 1, when a hardness measuring probe 4 inserted through a trocar 3 into an abdominal wall 2 of a human body 1 is contacted at the tip with a living body structure 5 and is moved so as to rub the surface with a proper pressure, a delicate hardness variation will be detected by a built-in pressure sensor 6 and will be transmitted to a measuring device 8 through a connecting cord 7 so that the peak value may be recorded and indicated in such a proper unit as g./mm$^2$., m.bar or mm.Hg in an indicating part 9 or that such hardness distribution curve 10A as is shown in FIG. 2 may be recorded on a recording sheet 10 by an XY plotter as shown in FIG. 2.

Figure 4:
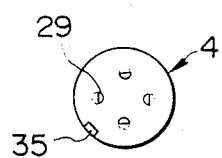
FIG. 4 is a plan view of FIG. 3.
Figure 3:
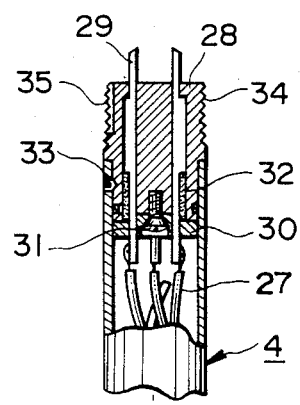
FIG. 3 is a vertically sectioned view showing the structure of the first embodiment.

The first embodiment shall be explained in detail in the following with reference to FIGS. 3 to 5. In the hardness measuring probe 4 of the first embodiment shown as magnified in FIG. 3, a substantially pipe-shaped thick tip member 12 having a step part of an inside diameter slightly expanded at both ends is secured to the tip side of an elongated (probe) outer tube 11, a pressure sensor 6 is fitted into the step part and is fixed, as required, by using a bonding agent, a fine diameter part in which the inside diameter of the tip member 12 on the side facing one pressure receiving surface 6A is of a fixed length is provided and a piston shaft 14 fitted with a sealing member 13 is fitted in this fine diameter part. A pressure chamber 15 sealed on both sides of the hollow part of the tip member 12 with the above mentioned pressure sensor 6 and the base end part of the piston shaft 14 fitted with the sealing member 13 is formed so that the pressure P$_3$ of this pressure chamber 15 may vary with the sliding movement (vertical movement in the illustration) of the piston shaft 14 and may act on the pressure receiving surface 6A (on one side) of the pressure chamber 15.

The above mentioned piston shaft 14 has a projection 16 formed on the outer periphery substantially in the middle portion. On the other hand, the tip member 12 is made thin on the tip side so as to have a stepped recess of a large diameter to be able to contain this projection 16 in contact. A coil spring 17 is fitted in the recess of the large diameter inward of the projection 16 on the outer periphery of the above mentioned contained piston shaft 14. This coil spring 17 is always in contact with the projection 16 of the piston shaft 14 so as to bias the piston shaft 14 toward the tip (downward in the illustration) in the axial direction of the probe 4. On the other hand, as a stopper to prevent this piston shaft 14 from springing out of the recess of the large diameter, a substantially ring-shaped tip piece 18 having as an inside diameter the diameter of the piston shaft 14 is fixed to the tip member 12. A member such as a roller 20 is rotatable mounted on an angled surface of the piston shaft 14 by means of a rotary shaft 19.

Figure 5:
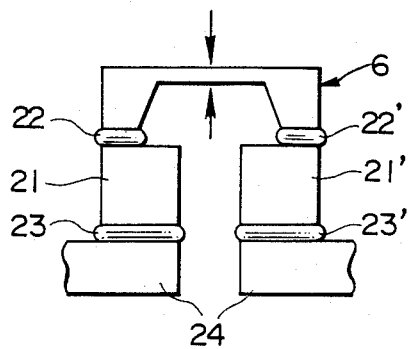
FIG. 5 is an explanatory view showing the basic structure of a pressure sensor used in the first embodiment.

On the other hand, the basic structure of the pressure sensor 6 is as shown in FIG. 5. That is to say, a semiconductor such as silicon is formed to be of a diaphragm type as a pressure receiving surface for pressure detection by utilizing the piezoresistance effect that the specific pressure of the semiconductor will vary with the pressing forces acting on both surfaces (both upper and lower surfaces in the illustration) and is secured in both end parts to base seats 21 and 21' with bonding agents 22 and 22'. These base seats are further secured to a package 24 with bonding agents 23 and 23' to form the pressure sensor of the diaphragm type so that the pressure acting on the respective pressure receiving surfaces as indicated by the arrows may be detected as variations of the resistance values formed in the form of the Wheatstone bridge in the diaphragm type silicon.

In the above mentioned pressure sensor 6, the pressure receiving surface 6A on one side faces the above mentioned pressure chamber 15 and the pressure receiving surface on the other side receives a pressure P$_2$ on the outer periphery of the outer tube 11 from a communicating hole 26 provided in the outer tube 11 side part or the like through a fine guide tube 25 formed on the base side of the pressure sensor 6 so that this pressure P$_2$ may be measured. The signals corresponding to the pressure values acting on the pressure receiving surface 6A on one side and the pressure receiving surface on the other side are led to respective contacts 29 provided in a short columnar supporting member 28 fixed to the base side end of the outer tube 11 through signal cords 27. In the supporting member 28, a lid 30 is fixed with a screw 31 or the like to the end surface on the side fitted in the outer tube and the respective bar-shaped contacts 29 projecting on both sides are pressed in and fixed through the supporting member 28 to which this lid 30 is fitted. the respective contacts 29 are cut to be step-shaped on both end part sides so that, on the rear end side (in the lower side end part in the illustration) when pressed in, the outer tube 11 to which the supporting member 28 is fitted will be sealed and intercepted inside and outside with respective sealing members 32.

The supporting member 28 is fixed with a screw 33 or the like from the side part fitted in the outer tube 11. A threaded part 34 is formed on the outer peripheral surface projecting rearward (outward) of the outer tube 11, and a positioning groove 35 is formed in a part of the outer periphery of the rear end of the outer tube 11. In operation, the electric signals corresponding to the pressing forces transmitted to the measuring device 8 through the connecting cord 7 provided with a connector screwed to the threaded part 34 and detected by the pressure receiving surface 6A on one side within the hardness measuring tube 4 and the pressure receiving surface on theother side receiving the pressure P$_2$ outside the outer tube 11 through the communicating hole 26 may be simultaneously indicated or the measured value on the other side may be automatically deducted from the measured value on one side and may be indicated.

The operation of the thus formed first embodiment shall be explained in the following.

First of all, the connecting cord 7 provided with the connector as shown in FIG. 1 is fitted to the rear end base side of the hardness measuring probe 4. The measuring probe 4 is then inserted through the abdominal wall 2 while guided by the trocar 3 and the roller 20 at the tip of the hardness measuring probe 4 is contacted under a proper pressure with the surface in an object position of a living body structure 5 or the like within a body cavity. The pressure sensor 6 used in this case is so made as to be able to measure the respective pressure values or not only the pressure $P_3$ acting on one pressure receiving surface 6A facing the pressure chamber 15 but also the pressure $P_2$ in the abdominal cavity (inflated with air) into which the probe is inserted led onto the other pressure receiving surface through the fine tube 25. Therefore, these pressure values can be simultaneously indicated by the indicating part 9 or can be recorded by an XY plotter or the like. It can be indicated by the indicating part 9 that the pressure $P_2$ value on the other is deducted in advance from the pressure $P_3$ value measured on one pressure receiving surface 6A or, as shown in FIG. 2, the measured results can be continuously recorded on a recording sheet by an XY plotter or the like.

When the roller 20 is moved to rub an object position with a proper pressing force, the roller 20 will rotate and move, a pressing force will act on the piston shaft 14 in response to the hardness of the position contacted by the roller 20 and the coil spring 17 will be extended or contracted against its biasing force to moe the piston shaft 14 up and down vertically along the axial direction of the outer tube 11. This vertical movement will be transmitted to the pressure chamber 15 and the pressure $P_3$ of the pressure chamber 15 will be proportional to the force pressing the piston shaft 14 or the roller 20. Therefore, if the pressure $P_3$ of the pressure chamber 15 acting as shown by the arrow on the pressure receiving surface 6A on one side is measured, the hardness of the object position will be able to be continuously measured by a simple operation.

In this embodiment, not only the hardness of the contacted position but also the pressure $P_2$ within the abdominal cavity can be measured or this pressure $P_2$ component can be automatically deducted. Therefore, the hardness of the object position can be easily measured at a high precision without being influenced by the fluctuation of the pressure $P_2$ within the body cavity. There is no need of measuring by repeating contact and separation as in the conventional example. Thus, the bad influence of the fluctuation of the pressing force in the case of the contact can be dissolved and the measuring precision can be improved. Therefore, there is an effect that the delicate hardness difference between the affected part and normal part around the object position can be also detected. Further, as the hardness measuring probe 4 is of a sealed structure, it can be used not only within an abdominal cavity inflated with air but also within a bladder containing circulated water. Also, as the hardness measuring probe 4 can be separated from the connecting cord 7, it can be easily sterizized.

Further, as the roller rotates in contact with the part contacting the object position, not only on a flat surface but also on an irregular surface, the hardness can be continuously measured with the reduced fluctuation of the pressing force. Also, as the sealed pressure chamber 15 is provided, the force acting on the pressure sensor 6 will be a uniform pressure and the pressure sensor 6 will be little worn, deformed or broken and can be used for a long time. As the roller 20 contacting the object to be measured rotates in contact, it will not be partly worn, deformed or broken and will be able to be used for a long time.

Figure 6:
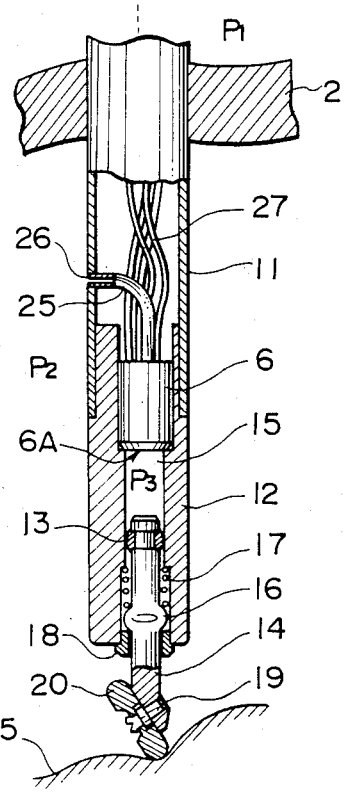
FIG. 6 is a vertically sectioned view showing an essential part on the tip side in a second embodiment of the present invention.

FIG. 6 shows a second embodiment wherein, instead of the coil spring 17 in the first embodiment, an elastic member 41 having a proper softness is contained in the pressure chamber 15.

In FIG. 6, the elastic member 41 molded of a foaming plastic or rubber material so as to contact the pressure receiving surface 6A on one side of the pressure sensor 6 and the rear end surface of the piston shaft 14 is contained within the pressure chamber 15 so that the piston 14 contacted by this elastic member 41 may be always biased toward the tip in the axial direction of the outer tube 11. A flange-shaped projection 16' contacting on the outer peripheral surface with the inner peripheral surface of the large dameter recess is formed on the substantially middle portion of this piston shaft 14. The extent of movement of the shaft 14 is prevented by abutment of the projection 16' against the tip piece 18 which acts as a stopper.

In this embodiment, when the elastic member 41 having a proper softness is pressed and deformed, the hardness of the contacted object position will be transmitted to the pressure receiving surface 6A on one side of the pressure sensor 6 as indicated by the arrow. The operation and effect of this second embodiment are substantially the same as of the first embodiment.

Figure 7:
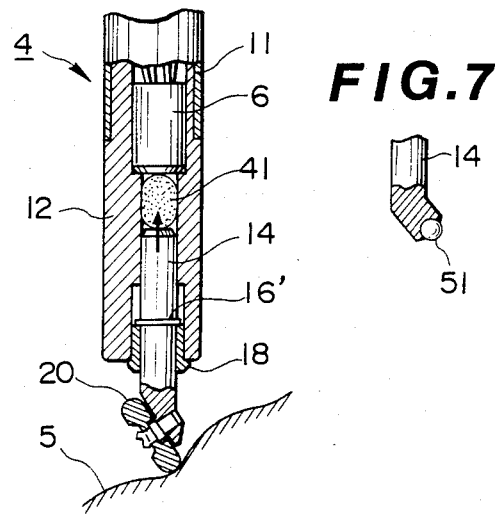
FIG. 7 is a vertically sectioned view showing the tip of a piston shaft in a third embodiment of the present invention.

FIG. 7 shows a third embodiment wherein a hemispherical or the like recess if formed in the tip part of the piston shaft 14 and a ball 51 is rotatably fitted in this recess.

The operation and effect of this embodiment are the same as of the above described embodiment.

In each of the above described embodiments, the diaphragm type pressure sensor 6 is used but, in some case, two ordinary pressure sensors can be used. In such case, the first pressure sensor will be fixed as the diaphragm type pressure sensor 6 is fitted and the pressure $P_2$ on the outer periphery of the outer tube 11 will be received on the pressure receiving surface of the second pressure sensor through such fine tube 25 as is described above or through such aperture as the communicating hole 26 provided in the side part or the like of the outer tube 11 instead of through the fine tube 24. This received pressure $P_2$ will be measured and will be indicated (recorded) in the ssame manner as in the value measured by the first pressure sensor or the value measured by the second pressure sensor will be deducted from the value measured by the first pressure sensor and the influence caused by this pressure fluctuation will be able to be automatically dissolved and indicated.

By the way, the above described hardness measuring probe 4 can be used not only to measure the hardness and pressure in the therapeutic field but also to measure the hardness and pressure in the industrial field.

Further, in each of the above described embodiments, the measured object pressing force is made to act on the pressure receiving surface 6A on one side of the pressure sensor 6 through such member showing a soft elastic property as of a gas or solid. However, in the case of measuring only a slight pressing force, the (rear) end surface of the piston shaft 14 facing the pressure chamber 15 will be able to be made to act in direct contact with the pressure receiving surface 6A.

Further, in each of the above described embodiments, the roller 20 or ball 51 rotating in contact is provided in the tip part of the piston shaft 14. However, in some case, the piston shaft 14 may be molded to be round in the tip part so as to slide in contact with the surface of the object to be measured.

The above described present invention can keep a comparatively stable contact with the surface of the measured object which may have recesses and projections and makes it possible to quickly and easily measure the hardness at a comparatively high precision.

Further, in the present invention, the part of the tip member 12 must be formed of a hard member but the outer tube 11 can be formed of a flexible member and therefore can be inserted through a somewhat curved inserting path to measure the hardness within. Thus the probe is adapted to a wide range of uses.

The hardness measuring probe can be inserted through the forceps channel of not only a hard endoscope but also a soft endoscope to measure the hardness of the inside wall or the like of an internal organ within a body cavity.

Further, if the direction of fitting the roller 20 or ball 51 in the piston shaft 14 is varied or is made variable (the part of the tip member 12 may be made curvable from the part toward the base from it), the hardness of the surface in a very wide range around the inserted part will be able to be measured at a high precision.

I claim:

1. A hardness measuring probe comprising
   a tip member;
   a pressure sensor mounted in said tip member and having a first pressure receiving surface on one side and a second pressure receiving surface on an opposite side;
   a shaft slidably mounted in and projecting from said tip member, said shaft being disposed opposite from said first pressure receiving surface to effect a change in pressure on said first pressure receiving surface in response to relative movement between said shaft and said tip member;
   a member rotatably mounted on said shaft for rollably contacting an object to be measured; and
   a tube having said tip member fitted therein and having an aperture communicating said second pressure receiving surface of said sensor with the exterior of said tube.

2. A probe as set forth in claim 1 wherein said member is a roller.

3. A probe as set forth in claim 1 wherein said member is a ball.

4. A probe as set forth in claim 1 wherein said sensor is a diaphragm type sensor.

5. A probe as set forth in claim 1 wherein said tube is closed at an end remote from said tip member.

6. A probe as set forth in claim 1 which further comprises a connector for a signal line removably connected to said tube for transmitting signals corresponding to the pressures detected on said pressure receiving surfaces of said sensor.

7. A probe as set forth in claim 1 which further comprises a sealed pressure chamber between said shaft and said sensor.

8. A probe as set forth in claim 7 wherein said chamber contains a gas.

9. A probe as set forth in claim 7 wherein said chamber contains a soft elastic member.

* * * * *

UNITED STATES PATENT AND TRADEMARK OFFICE
CERTIFICATE OF CORRECTION

PATENT NO. : 4,503,865

DATED : March 12, 1985

INVENTOR(S) : YOSHIO SHISHIDO

It is certified that error appears in the above-identified patent and that said Letters Patent is hereby corrected as shown below:

Column 5, line 58, change "sterizied" to -sterilized-

Column 6, line 44 change "24" to -25-

Column 7, line 3 change "above described present invention" to -invention thus provides a probe that--

Signed and Sealed this

First Day of October 1985

[SEAL]

Attest:

Attesting Officer

DONALD J. QUIGG

Commissioner of Patents and Trademarks—Designate